(12) United States Patent
Sander

(10) Patent No.: US 7,961,385 B2
(45) Date of Patent: Jun. 14, 2011

(54) LIGHT MICROSCOPE

(75) Inventor: Ulrich Sander, Rebstein (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 112 days.

(21) Appl. No.: 12/256,856

(22) Filed: Oct. 23, 2008

(65) Prior Publication Data

US 2009/0109524 A1    Apr. 30, 2009

(30) Foreign Application Priority Data

Oct. 25, 2007  (DE) .......................... 10 2007 051 405

(51) Int. Cl.
*G02B 21/18* (2006.01)
*G02B 21/00* (2006.01)

(52) U.S. Cl. .......................... 359/373; 359/368; 359/372

(58) Field of Classification Search ........... 359/368–390
See application file for complete search history.

(56) References Cited

U.S. PATENT DOCUMENTS

| | | | |
|---|---|---|---|
| 4,217,025 A * | 8/1980 | Takenaka | 359/377 |
| 4,605,287 A | 8/1986 | Lang et al. | |
| 5,132,837 A * | 7/1992 | Kitajima | 359/374 |
| 5,856,883 A | 1/1999 | Sander | |
| 6,282,021 B1 * | 8/2001 | Yano | 359/415 |
| 6,982,825 B2 | 1/2006 | Sander | |

FOREIGN PATENT DOCUMENTS

AT    20299    6/1905

* cited by examiner

*Primary Examiner* — Thong Nguyen
(74) *Attorney, Agent, or Firm* — Hodgson Russ LLP

(57) ABSTRACT

An assistant microscope add-on device for a surgical microscope (1) comprises an objective (22) inclined relative to an object plane (10) with an object field (10'), wherein the objective defines an objective plane (22') and an objective axis (16') perpendicular thereto forming an angle α larger than 0° to the surface normal of the object plane (10). A tube (23) and an eyepiece (24) having an eyepiece lens (27) defining an eyepiece plane (27') and an eyepiece axis (35) perpendicular thereto. Due to the oblique viewing angle, an intermediate image plane (26) to be imaged by the eyepiece (24) is inclined relative to the objective plane (22'). The resulting aberration is eliminated by the eyepiece axis (35) and the objective axis (16') forming an angle β of larger than 0°, wherein the angle β is so chosen that the eyepiece axis (35) is substantially perpendicular to the intermediate image plane (26). Consequently, the object field (10') is imaged free of distortion and sharply across the entire image area.

13 Claims, 3 Drawing Sheets

LIGHT MICROSCOPE

CROSS REFERENCE TO RELATED APPLICATIONS

This application claims priority of the German patent application 10 2007 051 405.2 filed Oct. 25, 2007 which is incorporated by reference herein.

FIELD OF THE INVENTION

The invention relates to a light microscope of a type including an objective that is inclined relative to an object plane having an object field. The invention relates in particular to a stereo microscope as a secondary observer unit, which is used as an add-on to a primary observer microscope, such as, for example, a so-called assistant microscope used as an add-on to a surgical microscope.

BACKGROUND OF THE INVENTION

Surgical microscopes used in medicine, and here in particular in ophthalmology and neurosurgery should provide the means for an assistant (secondary observer) to view the same field of operation as the surgeon (primary observer). In this connection it is known to fit an independent assistant microscope on the outside of a main microscope housing. Usually, both microscopes are designed as stereo microscopes and each comprise two completely separate beam paths through which the object can be viewed from two different directions so that a stereoscopic impression is created. Both main and assistant microscope have one objective each made up of one lens or a group of lenses. The primary observer views the object or the object plane substantially vertically from above, in which the object plane runs parallel to the object plane defined by the objective or perpendicular to its optical axis. Thus the illuminated object field can be sharply imaged across its entire surface by the objective and the following eyepiece into the observer's eye.

In the case of the secondary observer the problem exists that due to reasons of space the objective assigned to him has to be arranged laterally from the primary observer's objective. So that the same object field can be imaged, the viewing direction of the secondary observer is abnormal to the object plane and runs at an angle of typically 10-30° to the normal. For one thing, this means that the object field cannot be sharply imaged as a whole and for the other that it is perspectively distorted due to the angular viewing angle.

Such aberration in the secondary observer beam path can be avoided by using microscopes where primary and secondary observer look vertically onto the object through the same objective along a mutual axis. Such microscopes are for example known from DE-C 43 31 635 (corresponds to U.S. Pat. No. 5,856,883) and DE-C 33 33 471 (corresponds to U.S. Pat. No. 4,605,287). In accordance with DE-C 43 31 635 the light coming from the object is split up between primary and secondary observer after passing the shared objective by means of a beam splitter. The secondary observer beam path is laterally uncoupled. On the microscope in accordance with DE-C 33 33 471, the beam paths are split by means of a splitting plate. In both cases a loss in light intensity is accepted. Another difficulty with such integrated devices is the complex mechanics which is necessary to be able to pivot the assistant microscope between various positions (to the right and left of the main microscope).

Assistant microscopes with their own objective to be fitted on the outside of the housing of a main microscope present an inexpensive and mechanically easy-to-do alternative to the above-mentioned integrated devices. With such devices, which have been known since the 1980s, the aberration brought about by the oblique viewing angle mentioned earlier in this document, have so far been accepted. Similar problems also exist with microscopes which for other reasons look onto an object with an objective that is arranged angular to the object plane.

The Scheimpflug principle for the sharp imaging of an object plane that is at a relative angle to the objective, which is known from cartography and photography, going back to the AT-PS 20299 from the year 1905, applies on principle for determining the position of the intermediate image plane in the case of a lens. This principle states that to attain a sharp image, the image plane is inclined in such a way that its line of intersection with the image-side principal plane of the lens is equidistant to the optical axis as the line of intersection between the object plane and the object-side principal plane. Applied to a microscope without tube lens this means that object, objective and intermediate image plane approximately intersect in a straight line. On a microscope with infinite optical system with an objective, a tube lens and approximately parallel beams in-between, the planes of the objective and the tube lens roughly correspond to those principal planes mentioned above.

SUMMARY OF THE INVENTION

Thus the object of the invention is to provide a light microscope which achieves an improved imaging quality in the case of an oblique viewing angle.

The objective is achieved by a light microscope with the features described herein. Advantageous developments of the invention are evident from the dependent claims, the description and the drawings.

Particularly the light microscope used as the assistant microscope comprises at least one objective that is arranged at a relative angle to an object plane, in which the objective defines a main plane (objective plane) and an objective axis that is perpendicular to it and that runs at an angle $\alpha$ of larger than 0° to the surface normal of the object plane. It can, for example, be disposed angularly to the object plane at a fixed angle of inclination using an adequate mounting fixture. In the case of the assistant microscope, for example, it is disposed on the outside of a main surgical microscope or its stand at a fixed angle to the viewing direction of the main microscope.

The microscope further comprises at least one, in the case of a stereo microscope two eyepieces with at least one eyepiece lens which defines one eyepiece plane and one eyepiece axis perpendicular to it. The viewing by the secondary observer occurs along this eyepiece axis. Due to the angular position of the objective, the intermediate image plane created by the objective, possibly in conjunction with a downstream optical system (zooming system, tube lens(es)), which is to be projected into the observer's eye by the eyepiece, is arranged at a relative angle to the objective plane.

The term objective or eyepiece is also understood to comprise an objective system and an eyepiece system respectively.

According to the invention, the eyepiece is disposed on the housing in such a way that contrary to conventional microscopes the eyepiece axis on the invention does not run parallel to the objective axis but forms an angle $\beta$ of larger than 0° with it. The angle $\beta$ is so chosen that the eyepiece axis is substantially perpendicular to the intermediate image plane.

As already known, the beam path can be deflected by beam deflecting opto-mechanical means, for example, in order to provide better working conditions at the microscope or achieve a lower overall height. The previously-mentioned angles α and β as well as the previously-mentioned axes and planes are those in the straight condition of the beam path, i.e. the beam path is not deflected by means of opto-mechanical elements such as mirrors or beam splitters.

The measure according to the invention eliminates distortion in the image observed in a surprisingly simple manner, rendering a sharp image as a whole and across the entire object area while gaining full depth of field. Apart from the different viewing angle, the secondary observer sees the same image in the same optical quality on the assistant microscope as the primary observer.

Using known methods, such as a computer, for example, the exact position of the intermediate image plane can be calculated on the basis of the position and optical properties of the objective, and, where applicable, further optical elements such as tube lenses, zooming systems. On the basis of this, the angle of inclination β can then be calculated.

BRIEF DESCRIPTION OF THE DRAWINGS

Exemplary embodiments of the invention are shown in the drawing and described in further detail in the ensuing description, wherein.

DETAILED DESCRIPTION OF THE INVENTION

Figure 1:
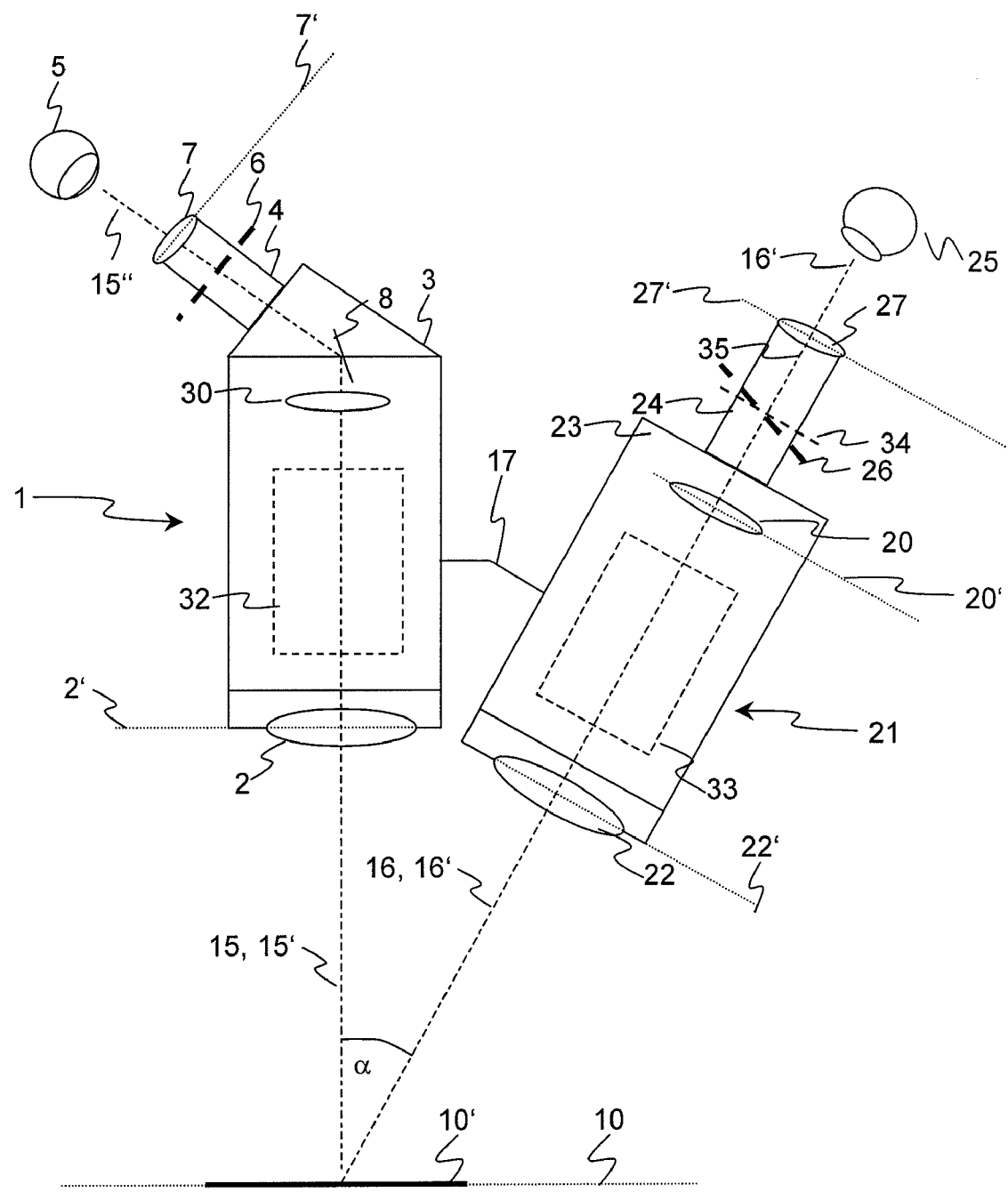
FIG. 1 is a schematic view of a main microscope having an assistant microscope according to the state of the art.
Figure 2:
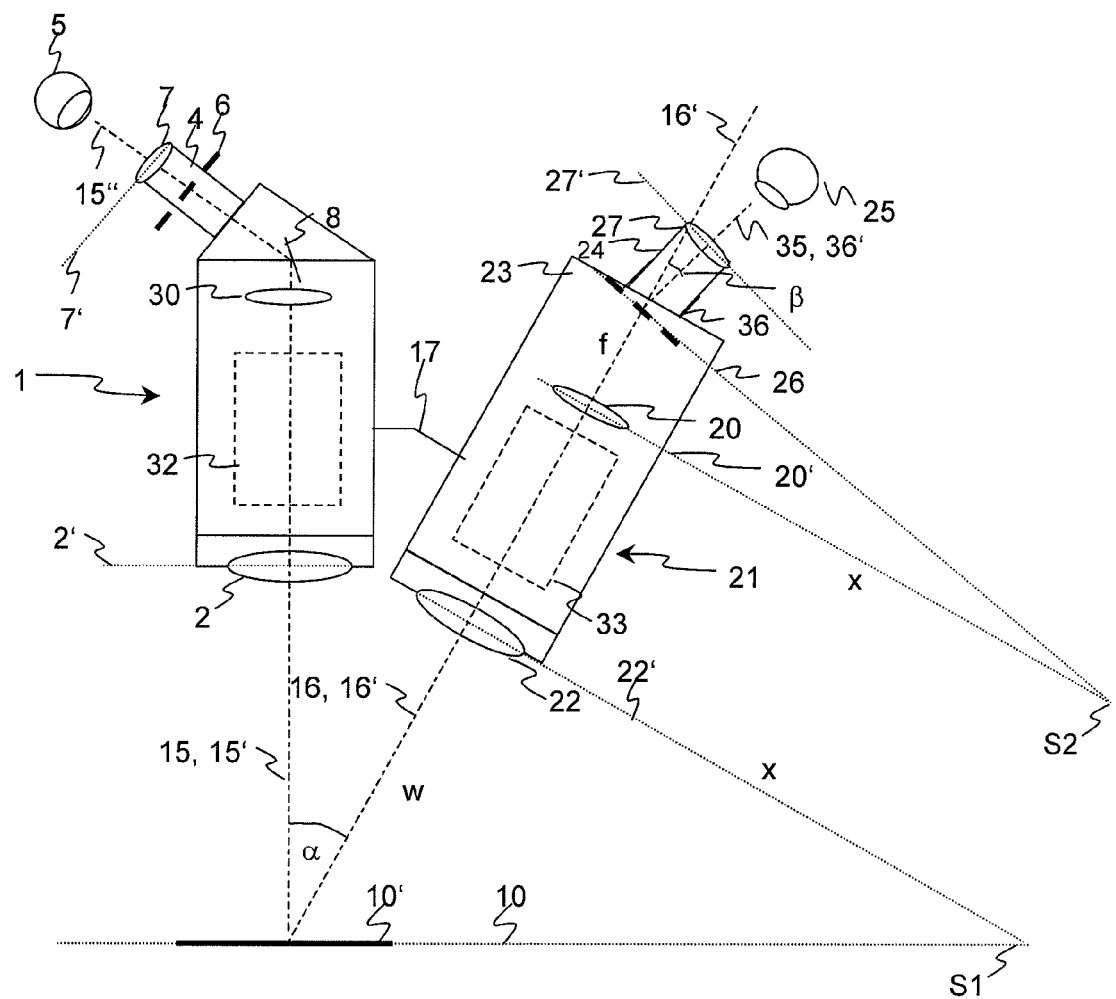
FIG. 2 is a schematic view of a main microscope having an assistant microscope according to the invention in accordance with a first variant of the invention.
Figure 3:
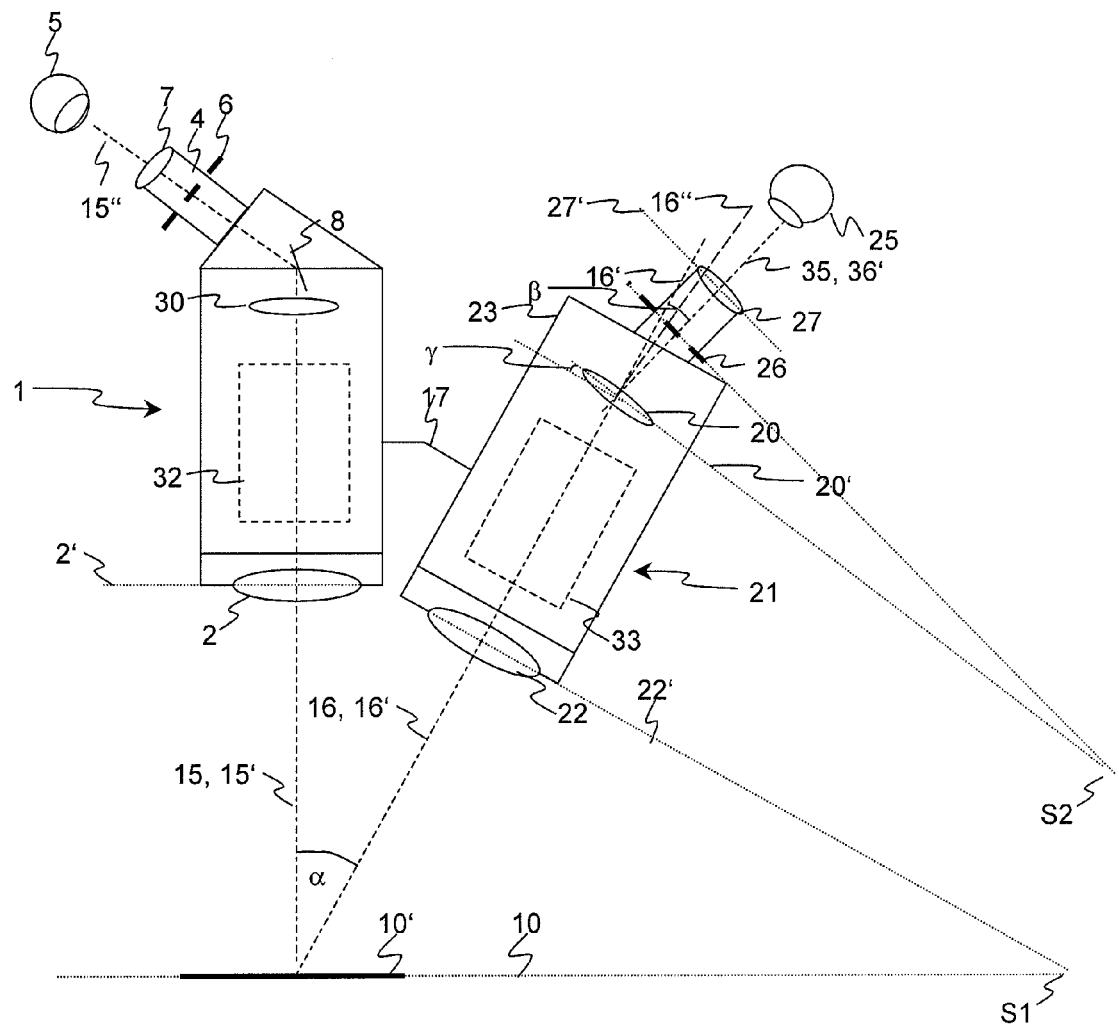
FIG. 3 is a schematic view of a main microscope having an assistant microscope according to the invention in accordance with a second variant of the invention.

FIGS. 1 to 3 show the schematic structure of a main microscope 1 having an assistant microscope 21. The assistant microscope 21 is attached to the outside of the main microscope 1 at a fixed angle by means of a mounting fixture 17; preferably pivotable around the viewing axis 15, 15' of the main microscope 1. The main and assistant microscope 1, 21 are in particular concerned with stereo microscopes that are used as surgical microscopes, wherein in each case only one of the two stereoscopic beam paths is shown here.

In the object plane 10 a normally circular object field 10' is illuminated with incident light illumination by a lighting device that is not shown here. The light of the object from the object field 10' is imaged via the objective 2 of the main microscope 1 inside the binocular tube 3 via a tube lens 30 in the eyepiece intermediate image plane 6. From there the intermediate image in the intermediate image plane 6 is projected via the eyepiece 4 with eyepiece lens 7 into the eye 5 of the primary observer.

The microscope is a microscope with an infinite optical system. Here the object plane 10 is at a single focal distance from the objective 2 so that the light coming from the object points passes through the afocal area between tube lens 30 and objective 2 as almost parallel beam bundles and is imaged by the tube lens 30 in its focal plane (intermediate image plane 6). Additional optical elements such as in particular a zooming system 32 for setting the zoom may be provided in the afocal area between objective 2 and tube lens 30.

The primary viewing direction 15 corresponds to the axis 15' of the objective 2. It is perpendicular to the object plane 10. Thus the intermediate image plane 6 is parallel to the principal plane of the objective 2 (objective plane 2') and to the principal plane of the eyepiece 7 (eyepiece plane 7'), and the entire object field is sharply projected to the eye 5 of the primary observer. For ergonomic reasons, the beam path inside the binocular tube 3 may be deflected by beam-deflecting means 8 in a manner known per se; the eyepiece plane 7' is then oriented perpendicular to the deflected axis 15''. Normally, there is an eyepiece aperture in the intermediate image plane 6, which provides for a defined edge of the viewed image.

The assistant microscope 21 has the same structure as the main microscope 1 in accordance with the state of the art (FIG. 1) and also comprises an objective 22, a binocular tube 23, a tube lens 20 and an eyepiece 24 having an eyepiece lens 27. It projects the light of the object from the object plane 10 via the objective 22 via the binocular tube 23 to the eyepiece intermediate image plane 26. From there the eyepiece lens 27 of the eyepiece 24 projects the light into the eye 25 of the secondary observer. Here too, for example, a zooming system 33 may be provided between objective 22 and tube lens 20.

Due to the lateral mounting on the main microscope 1, the assistant microscope 21 is inclined toward the object plane 10. Its viewing direction 16 or more precisely the axis 16' of the objective 22 forms together with the main viewing direction 15 an angle α of typically 10-30°. In this way the object plane 10 is imaged by the objective 22 in an intermediate image plane 26 which is no longer perpendicular to the axis 16 or 16'. Only the nominal intermediate image plane 34, which is at about a single focal distance from the eyepiece lens 27, is sharply projected to the eye by the eyepiece 24. Due to the angled setting, the image in the actual intermediate image plane 26 no longer concurs with this nominal intermediate image plane 34. Therefore the image is rendered significantly more out of focus than is the case for the primary observer and what is more, in addition it is perspectively distorted.

As shown in FIG. 2, this undesired effect can be eliminated in accordance with the invention by viewing the intermediate image plane 26 by means of the eyepiece 24 or more precisely the eyepiece lens 27 via an eyepiece axis 35, which is perpendicular to the inclined actual intermediate image plane 26. As a result the full definition across the entire image is achieved again and perspective distortion of the image is eliminated.

The position of the intermediate image plane and thus the angle β can be approximately determined as follows: The microscope has an infinite optical system where the image generated by the objective 22 is created at infinity. The beams coming from one object point in the focal plane (focal distance w) exit the objective as a virtually parallel bundle, which is merged into a real pixel by the tube lens 20 (or the tube system) aligned parallel to the objective 22 in its focal plane (focal distance f). The intermediate image is projected into the eye by the eyepiece 24. The objective 22 and tube lens 20 of the assistant microscope 21 act together like an objective having a finite focal distance with principal planes, which are approximately defined by the objective plane 22' and tube lens plane 20'. The line of intersection S1 of object plane 10 and objective plane 22' is at a distance x from the axis 16. According to the Scheimpflug principle the line of intersection S2 of the tube lens plane 20' and 20 of the inclined intermediate image plane 26 has the same distance x from the axis 16. The inclination of the viewing axis 16 relative to the viewing direction 15 of the primary observer is defined by the angle α, which is predetermined by the mounting of the assistant microscope. It applies x=w/tan(α)=f/tan(β), thus β=arctan((f/w)*tan(α)).

Preferably the binocular tube 23 for the insertion of in particular standard eyepieces has cylindrical sleeves 36, the cylinder axis of which are inclined by the angle β toward the objective axis 16'. As a result, when inserting the eyepieces 24 into the sleeves 36 they are already oriented so that their eyepiece axis 35 provides the correct angle of inclination to project the intermediate image 26 into the eye 25 of the secondary observer without distortion.

Preferably the intermediate image is created inside the binocular tube 23 in order to cut off as little as possible of the light coming from the edge areas of the object field 10' and with this achieve an image that is as vignette-free as possible.

A further embodiment is shown in FIG. 3. Here, the tube lens 20 or more precisely its plane 20' is already inclined by an angle γ relative to the objective 22 or more precisely the objective plane 22'. Due to the inclined tube lens 20, the axis 16 of the assistant microscope 21 is deviated in contrast to the case of FIG. 2; the new axis given the reference number 16". In this way the position of the intermediate image plane 26 is modified relative to the case with a tube lens 20 that is aligned parallel to the objective 22. Consequently, the Scheimpflug principle can now be approximately expressed as follows: The distance x of the line of intersection S1 between the objective plane 22' and the object plane 10 of the initial optical axis 16 corresponds to the distance x of the line of intersection S2 between the inclined tube lens plane 20' and the intermediate image plane 26 of the deviated axis 16".

Thus the angle β between the eyepiece axis 35 and the initial axis 16, 16' is smaller than in the case of FIG. 2. This variant has advantages with regard to an imaging of the object field 10' which is as vignette-free as possible thanks to the inclined eyepiece 24.

The embodiments which have been described herein can analogously also be used with microscopes having a finite optical system, i.e. without tube lens. In the case of both finite and infinite optical systems, the position of the actual intermediate image plane 26 is preferably calculated taking all optical components in the beam path into account and the eyepiece 24 is arranged in such a way that the eyepiece axis 35 is aligned perpendicular to this actual intermediate image plane. In the case of a simple optical system, the position of the intermediate image plane as displayed in a simplified fashion in the above embodiments can be established in a geometric-optical approach on the basis of the Scheimpflug principle. In the case of more complex optical systems, the beam path is simulated in a manner known per se.

The beam path of the microscope can be unfolded in a manner known per se using beam-deflecting means. For example, beam-deflecting means can be provided, by means of which the beam path is deflected inside the tube perpendicular to the initial viewing direction. This is, for example, used to accommodate a zooming system and/or other optical components with the optical axis perpendicular to the objective axis in a space-saving manner, for example, as disclosed in DE-B 102 55 961 (corresponds to U.S. Pat. No. 6,982,825 B2).

Likewise, flexible optical waveguides may be arranged within the beam path between tube lens and eyepiece, in order to provide a moveable tube with adjustable alignment of the eyepieces without changing the effective viewing angle, for example, as described in DE 105 03 463. It should be pointed out here, that the optical waveguides are arranged in such a way that the observer looks vertically down on the inclined intermediate image plane.

Furthermore, the beam path can be deflected in the eyepiece side end part of the tube in a manner known per se using mirrors or the like. Here too, it should be pointed out that the eyepiece is arranged in such a way that its axis is perpendicular to the inclined intermediate image plane now imaged by the mirror.

The effective viewing angle is not changed by the above-described beam deflection, i.e. the observer continues to look "from above" or "from the side" onto the object and the intermediate image plane, even if the eyepiece is tilted in relation to the tube and/or the beam path is directed through the laterally disposed zooming system. As mentioned above, the above-described angles α and β are to be defined without said deflection using opto-mechanical deflection elements.

LIST OF REFERENCE NUMBERS

1 Main microscope
2 Objective of the main microscope
2' Objective plane of the main microscope
3 Binocular tube of the main microscope
4 Eyepiece of the main microscope
5 Primary observer
6 Eyepiece intermediate image plane of the main microscope
7 Eyepiece lens of the main microscope
7' Eyepiece plane of the main microscope
8 Deflection element
10 Object plane
15 Axis of the main microscope
15' Objective axis of the main microscope
15" Viewing axis of the main microscope deviated by a deflection element
16 Axis of the assistant microscope
16' Objective axis of the assistant microscope
16" Viewing axis of the assistant microscope deviated by the inclined tube lens
17 Mounting Fixture
20 Tube lens of the assistant microscope
20' Tube lens plane of the assistant microscope
21 Assistant microscope
22 Objective of the assistant microscope
22' Objective plane of the assistant microscope
23 Binocular tube of the assistant microscope
24 Eyepiece of the assistant microscope
25 Secondary observer
26 Eyepiece intermediate image plane of the assistant microscope
27 Ocular lens of the assistant microscope
27' Eyepiece plane of the assistant microscope
30 Tube lens of the main microscope
32, 33 Zooming system
34 Nominal intermediate image plane
35 Eyepiece axis of the assistant microscope
36 Sleeve
36' Sleeve axis
S1 Line of intersection 22' with 10
S2 Line of intersection 20' with 26

What is claimed is:
1. A light microscope (21) comprising:
an objective (22) inclined relative to an object plane (10) including an object field (10'), wherein the objective (22) defines an objective plane (22') and an objective axis (16') perpendicular to the objective plane, the objective axis (16') intersecting the surface normal of the object plane (10) in the object field to form an angle α greater than 0° with the surface normal of the object plane;

a tube (23); and at least one eyepiece (24) supported by the tube (23), each eyepiece (24) having at least one eyepiece lens (27) defining an eyepiece plane (27') and an eyepiece axis (35) perpendicular to the eyepiece plane (27'), wherein an intermediate image plane (26) to be imaged by the eyepiece (24) is inclined at a relative angle to the objective plane (22') and the intermediate image plane (26) is obliquely intersected by an observation beam path leading thereto;

wherein the eyepiece axis (35) forms an angle β with the objective axis (16') that is larger than 0°, wherein the angle β is so chosen that the eyepiece axis (35) is substantially perpendicular to the intermediate image plane (26).

2. The light microscope as claimed in claim 1, wherein the light microscope is an assistant microscope intended as an add-on device for a surgical microscope.

3. The light microscope as claimed in claim 1, wherein the light microscope (21) is a stereo microscope including a binocular tube and two eyepieces.

4. The light microscope as claimed in claim 3, wherein the light microscope (21) is a surgical microscope.

5. The light microscope as claimed in claim 1, further comprising a tube lens (20), wherein light coming from one point in a focal plane of the objective (22) is merged by the objective into a virtually parallel beam bundle and merged by the tube lens into a point in a focal plane of the tube lens.

6. The light microscope as claimed in claim 5, characterized in that for the angle β at least approximately the following relation applies: β=arctan((f/w)*tan(α)), wherein f is the focal distance of the tube lens and w the focal distance of the objective.

7. The light microscope as claimed in claim 5, wherein the tube lens plane (20') is inclined relative to the objective plane (22').

8. The light microscope as claimed in claim 1, further comprising a zooming system (33) arranged downstream from the objective (22).

9. The light microscope as claimed in claim 1, wherein the tube (23) includes at least one cylindrical sleeve (36) for retaining the at least one eyepiece (24), wherein a sleeve axis (36') of the cylindrical sleeve (36) and the objective axis (16') form the angle β.

10. The light microscope as claimed in claim 1, wherein tube (23) is formed and a length (L) of the eyepiece (24) is chosen such that despite the eyepiece axis (35) being inclined relative to the objective axis (16'), the object field (10') is imaged by the eyepiece (24) substantially vignette-free.

11. The light microscope as claimed in claim 1, wherein the light microscope is an assistant microscope further comprising a mounting fixture (17) by which the assistant microscope can be attached at a constant angle of inclination relative to a main microscope (1).

12. The light microscope as claimed in claim 11, wherein the mounting fixture (17) is rotatable or pivotable around a viewing axis (15) of the main microscope (1).

13. A microscope system comprising:

a main microscope (1) including an objective (2) having an objective plane (2') and an objective axis (15'), the objective plane (2') being aligned parallel to an object plane (10) and the objective axis (15') being aligned perpendicular to the object plane (10); a tube (3); and at least one eyepiece (4) supported by the tube (3), each eyepiece having at least one eyepiece lens (7); and an assistant microscope (21) including an assistant objective (22) inclined relative to the object plane (10), wherein the assistant objective (22) defines an assistant objective plane (22') and an assistant objective axis (16') perpendicular to the assistant objective plane, the assistant objective axis (16') intersecting the surface normal of the object plane (10) in the object field to form an angle α greater than 0° with the surface normal of the object plane; an assistant tube (23); and at least one assistant eyepiece (24) supported by the assistant tube (23), each assistant eyepiece (24) having at least one assistant eyepiece lens (27) defining an assistant eyepiece plane (27') and an assistant eyepiece axis (35) perpendicular to the assistant eyepiece plane (27'), wherein an intermediate image plane (26) to be imaged by the assistant eyepiece (24) is inclined at a relative angle to the assistant objective plane (22') and the intermediate image plane (26) is obliquely intersected by an observation beam path leading thereto; wherein the assistant eyepiece axis (35) forms an angle β with the assistant objective axis (16') that is larger than 0°, wherein the angle β is so chosen that the assistant eyepiece axis (35) is substantially perpendicular to the intermediate image plane (26);

wherein the angle α is a constant angle.

* * * * *